United States Patent
Heintzberger

(10) Patent No.: US 11,839,188 B2
(45) Date of Patent: Dec. 12, 2023

(54) LETTUCE VARIETY TETON

(71) Applicant: Sakata Seed America, Inc., Morgan Hill, CA (US)

(72) Inventor: John Heintzberger, Eagle, ID (US)

(73) Assignee: Sakata Seed America, Inc., Morgan Hill, CA (US)

( * ) Notice: Subject to any disclaimer, the term of this patent is extended or adjusted under 35 U.S.C. 154(b) by 13 days.

(21) Appl. No.: 17/447,095

(22) Filed: Sep. 8, 2021

(65) Prior Publication Data

US 2022/0078988 A1 Mar. 17, 2022

Related U.S. Application Data

(60) Provisional application No. 63/078,446, filed on Sep. 15, 2020.

(51) Int. Cl.
*A01H 5/12* (2018.01)
*A01H 6/14* (2018.01)

(52) U.S. Cl.
CPC ............ *A01H 6/1472* (2018.05); *A01H 5/12* (2013.01)

(58) Field of Classification Search
CPC ................................ A01H 6/1472; A01H 5/12
See application file for complete search history.

(56) References Cited

U.S. PATENT DOCUMENTS 10,271,501 B2 * 4/2019 Avila ....................... A01H 5/12

OTHER PUBLICATIONS

Mou. 2011. Mutation in Lettuce Improvement. International Journal of Plant Genomics. pp. 1-7. (Year: 2011).*
Pan et al. 2022. Establishment of an Efficient Genome Editing System in Lettuce Without Sacrificing Specificity. Frontiers in Plant Science. vol. 13: 1-8. (Year: 2022).*
Cheng et al. 2018. Enhancing growth rate of lettuce by mutating lettuce seeds with nuclear irradiation. Carbon Resources Conversion I: 55-60. (Year: 2018).*

* cited by examiner

*Primary Examiner* — Karen M Redden
(74) *Attorney, Agent, or Firm* — Weatherly IP Solutions, LLC; James M. Weatherly

(57) ABSTRACT

One embodiment relates to seed and plants of lettuce variety Teton. Another embodiment relates to the plants, seeds and tissue cultures of lettuce variety Teton, and to methods for producing a lettuce plant produced by crossing such plants with themselves, with another lettuce plant, such as a plant of another genotype, or with vegetatively propagating said plant. Another embodiment further relates to seeds and plants produced by such crossing. Further embodiments relate to parts of such plants, including the fruit and gametes of such plants.

24 Claims, No Drawings

LETTUCE VARIETY TETON

CROSS REFERENCE TO RELATED APPLICATIONS

The present application is a non-provisional application and claims priority to U.S. Provisional Application No. 63/078,446, as filed on Sep. 15, 2020, the entire contents of which are herein incorporated by reference for all they teach and disclose.

BACKGROUND

All publications cited in this application are herein incorporated by reference. Practically speaking, all cultivated forms of lettuce belong to the highly polymorphic species *Lactuca sativa* that is grown for its edible head and leaves. *Lactuca sativa* is in the Cichoreae tribe of the Asteraceae (Compositae) family. Lettuce is related to chicory, sunflower, aster, dandelion, artichoke, and chrysanthemum. Sativa is one of about 300 species in the genus *Lactuca*. There are seven different morphological types of lettuce. The crisphead group includes the iceberg and batavian types. Iceberg lettuce has a large, firm head with a crisp texture and a white or creamy yellow interior. The batavian lettuce predates the iceberg type and has a smaller and less firm head. The butterhead group has a small, soft head with an almost oily texture. The romaine, also known as cos lettuce, has elongated upright leaves forming a loose, loaf-shaped head and the outer leaves are usually dark green. Leaf lettuce comes in many varieties, none of which form a head, and include the green oak leaf variety. Latin lettuce looks like a cross between romaine and butterhead. Stem lettuce has long, narrow leaves and thick, edible stems. Oilseed lettuce is a type grown for its large seeds that are pressed to obtain oil. Latin lettuce, stem lettuce, and oilseed lettuce are seldom seen in the United States.

Presently, there are over one thousand known lettuce varieties. As a crop, lettuce is grown commercially wherever environmental conditions permit the production of an economically viable yield.

Lettuce, is an important and valuable vegetable crop. Thus, there is an ongoing need for improved lettuce varieties.

SUMMARY

According to one embodiment, there is provided a novel lettuce variety designated Teton (previously designated R86). Another embodiment also encompasses the seeds of lettuce variety Teton, the plants of lettuce variety Teton, plant parts of the lettuce variety Teton (including leaves, seed, gametes), methods of producing seed from lettuce variety Teton, and method for producing a lettuce plant by crossing the lettuce variety Teton with itself or another lettuce plant, methods for producing a lettuce plant containing in its genetic material one or more transgenes, and the transgenic lettuce plants produced by that method. Another embodiment also relates to methods for producing other lettuce plants derived from lettuce variety Teton and to lettuce plants, parts thereof and seed derived by the use of those methods. Another embodiment further relates to hybrid lettuce seeds and plants (and parts thereof including leaves) produced by crossing lettuce variety Teton with another lettuce plant.

In another aspect, another embodiment provides for regenerable cells for use in tissue culture of lettuce variety Teton. In another embodiment, the tissue culture is capable of regenerating plants having all or essentially all of the physiological and morphological characteristics of the foregoing lettuce plant and/or of regenerating plants having the same or substantially the same genotype as the foregoing lettuce plant. In another embodiment, the regenerable cells in such tissue cultures are meristematic cells, cotyledons, hypocotyl, leaves, pollen, embryos, roots, root tips, anthers, pistils, ovules, shoots, stems, petiole, pith, flowers, capsules and/or seeds as well as callus and/or protoplasts derived from any of the foregoing. Still further, another embodiment provides for lettuce plants regenerated from the tissue cultures of lettuce variety Teton. As used herein, the transitional phrase "essentially of" means that the scope of a claim is to be interpreted to encompass the specified materials or steps recited in the claim "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original). Thus, the term "consisting essentially of" when used in a claim or the description of one or more embodiments is not intended to be interpreted to be equivalent to "comprising."

Another embodiment provides for a method of producing lettuce seed, the method comprising crossing a plant of lettuce variety Teton with itself or a second lettuce plant. Another embodiment further provides that the method further comprises collecting the seed.

Another embodiment provides for methods for producing hybrids and other lettuce plants derived from lettuce variety Teton. Lettuce plants derived by the use of those methods are also part of the embodiments as well as plant parts, seed, gametes and tissue culture from such hybrid or derived lettuce plants.

In another embodiment, a lettuce plant derived from lettuce variety Teton comprises cells comprising at least one set of chromosomes derived from lettuce variety Teton. In another embodiment, a lettuce plant or population of lettuce plants derived from lettuce variety Teton comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from lettuce variety Teton, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of lettuce variety Teton. In another embodiment, the lettuce plant derived from lettuce variety Teton is one, two, three, four, five or more breeding crosses removed from lettuce variety Teton.

In another embodiment, a hybrid or derived plant from lettuce variety Teton comprises a desired added trait(s). In representative embodiments, a lettuce plant derived from lettuce variety Teton comprises all of the morphological and physiological characteristics of lettuce variety Teton (e.g., as described in Table 1). In another embodiment, the lettuce plant derived from lettuce variety Teton comprises essentially all of the morphological and physiological characteristics of lettuce variety Teton (e.g., as described in Table 1), with the addition of a desired added trait(s).

Another embodiment also relates to methods for producing a lettuce plant comprising in its genetic material one or more transgenes and to the transgenic lettuce plant produced by those methods (and progeny lettuce plants comprising the transgene). Also provided are plant parts, seed and tissue culture from such transgenic lettuce plants, optionally wherein one or more cells in the plant part, seed, or tissue culture comprises the transgene. The transgene can be introduced via plant transformation and/or breeding techniques.

Another embodiment provides for a single gene converted plants of lettuce variety Teton. Plant parts, seed, and tissue culture from such single gene converted plants are also contemplated by the one or more embodiments of the present application. The single transferred gene may be a dominant or recessive allele. In another embodiment, the single transferred gene confers such traits as male sterility, herbicide resistance, pest resistance (e.g., insect and/or nematode resistance), modified fatty acid metabolism, modified carbohydrate metabolism, disease resistance (e.g., for bacterial, fungal and/or viral disease), male fertility, enhanced nutritional quality, improved appearance (e.g., color), improved salt tolerance, industrial usage, or any combination thereof. The single gene may be a naturally occurring lettuce gene or a transgene introduced into lettuce through genetic engineering techniques. A single gene converted or conversion plant refers to a plant that is developed by plant breeding techniques (e.g., backcrossing) or via genetic engineering wherein essentially all of the desired morphological and physiological characteristics of a line are recovered in addition to the single gene transferred into the line via the plant breeding technique or via genetic engineering.

Another embodiment further provides for methods for developing lettuce plants in a lettuce plant breeding program using plant breeding techniques including, for example, crossing, recurrent selection, mutation breeding, wherein said mutation breeding selects for a mutation that is spontaneous or artificially induced, recurrent selection, crossing, open-pollination, backcrossing, pedigree breeding, double haploid techniques, restriction fragment length polymorphism enhanced selection, genetic marker enhanced selection and/or transformation. Seeds, lettuce plants, and parts thereof, produced by such breeding methods are also part of the embodiments of the present application.

Another embodiment provides for methods of multiplication or propagation of lettuce plants of the present embodiments, which can be accomplished using any method known in the art, for example, via vegetative propagation and/or seed.

Another embodiment further provides for a method of producing food or feed comprising (a) obtaining a lettuce plant of Teton, optionally wherein the plant has been cultivated to maturity, and (b) collecting at least one lettuce plant or part thereof (e.g., leaves) from the plant.

Additional embodiments include harvested products and processed products from the lettuce plants of Teton. A harvested product can be a whole plant or any plant part, as described herein. Thus, in some embodiments, a non-limiting example of a harvested product includes a seed, a leaf and/or a stem.

In another embodiment, a processed product includes, but is not limited to: cut, sliced, ground, pureed, dried, canned, jarred, washed, packaged, frozen and/or heated leaves and/or seeds of the lettuce plants of the embodiments, or any other part thereof. In a further embodiment, a processed product includes a sugar or other carbohydrate, fiber, protein and/or aromatic compound that is extracted, purified or isolated from a lettuce plant of one or more embodiments. In further embodiments, the processed product includes washed and packaged leaves (or parts thereof) of Teton.

The seed of Teton can be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

Another embodiment provides for a seed of lettuce variety Teton. As a further aspect, another embodiment provides for a plant of lettuce variety Teton.

An additional embodiment provides for a lettuce plant, or a part thereof, having all or essentially all of the physiological and morphological characteristics of a plant of lettuce variety Teton.

Another embodiment provides for leaves and/or seed of the lettuce plants of Teton and a processed product from the leaves and/or seed of the said lettuce plants.

Another embodiment provides for a method of producing lettuce seed, the method comprising crossing a lettuce plant of Teton with itself or a second lettuce plant. Another embodiment provides for a seed produced by this method and plants produced by growing the seed.

Another embodiment provides a method for producing a seed of a lettuce plant derived from lettuce variety Teton, the method comprising: (a) crossing a lettuce plant of lettuce variety Teton with a second lettuce plant; and (b) allowing seed of a lettuce plant derived from lettuce variety Teton to form. A further embodiment of the method comprises: (c) growing a plant from the seed derived from lettuce variety Teton of step (b); (d) selfing the plant grown from the lettuce seed derived from lettuce variety Teton or crossing it to a second lettuce plant to form additional lettuce seed derived from lettuce variety Teton, and (e) repeating steps (c) and (d) 0 or more times to generate further derived lettuce seed. Optionally, the method comprises: (e) repeating steps (c) and (d) one or more times (e.g., one to three, one to five, one to six, one to seven, one to ten, three to five, three to six, three to seven, three to eight or three to ten times) to generate further derived lettuce plants. As another option, the method can comprise collecting the seed. A further embodiment provides for seed produced by these methods and plants produced by growing the seed.

A further embodiment provides for a method of producing lettuce leaves, the method comprising: (a) obtaining a plant of lettuce variety Teton, optionally wherein the plant has been cultivated to maturity; and (b) collecting leaves from the plant. A further embodiment provides for the leaves produced by this method.

Another embodiment provides for a method of vegetatively propagating a plant of lettuce variety Teton. In a non-limiting example, the method comprises: (a) collecting tissue capable of being propagated from a plant of lettuce variety Teton; (b) cultivating the tissue to obtain proliferated shoots; and (c) rooting the proliferated shoots to obtain rooted plantlets. A further embodiment provides for growing plants from the rooted plantlets. Further embodiments also encompass the plantlets and plants produced by these methods.

Another embodiment provides a method of introducing a desired added trait into lettuce variety Teton, the method comprising: (a) crossing a first plant of lettuce variety Teton with a second lettuce plant that comprises a desired trait to produce $F_1$ progeny; (b) selecting an $F_1$ progeny that comprises the desired trait; (c) crossing the selected Fiprogeny with lettuce variety Teton to produce backcross progeny; and (d) selecting backcross progeny comprising the desired trait to produce a plant derived from lettuce variety Teton comprising a desired trait. In embodiments, the selected progeny comprises all or essentially all the morphological and physiological characteristics of the first plant of lettuce variety Teton. The method may further comprise: (e) repeating steps (c) and (d) one or more times in succession (e.g., one to three, one to five, one to six, one to seven, one to ten, three to five, three to six, three to seven, three to eight or three to ten times) to produce a plant derived from lettuce variety Teton comprising the desired trait.

Another embodiment provides for a method of producing a plant of lettuce variety Teton comprising a desired added trait, the method comprising introducing a transgene conferring the desired trait into a plant of lettuce variety Teton. The transgene can be introduced by transformation methods (e.g., genetic engineering) or breeding techniques. In embodiments, the plant comprising the transgene comprises all or essentially all of the morphological and physiological characteristics of lettuce variety Teton.

Another embodiment provides for lettuce plants produced by the methods of one or more embodiment, wherein the lettuce plant has the desired added trait as well as seed from such lettuce plants.

According to the foregoing methods, the desired added trait can be any suitable trait known in the art including, but not limited to, for example, male sterility, male fertility, herbicide resistance, insect or pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, industrial usage, or any combination thereof.

In further embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In further embodiments, a transgene conferring pest resistance (e.g., insect and/or nematode resistance) encodes a *Bacillus thuringiensis* endotoxin.

In further embodiments, transgenic plants, transformed plants, hybrid plants and lettuce plants derived from lettuce variety Teton have at least 3, 4, 5, 6, 7, 8, 9, 10 or more of the morphological and physiological characteristics of lettuce variety Teton (for example, as described in Table 1), or even all of the morphological and physiological characteristics of lettuce variety Teton, so that said plants are not significantly different for said traits than lettuce variety Teton, as determined at the 5% significance level when grown in the same environmental conditions; optionally, with the presence of one or more desired additional traits (e.g., male sterility, disease resistance, pest or insect resistance, herbicide resistance, and the like).

Tolerance to infections is defined as the ability of a host to limit the impact of parasites, pathogens or herbivores on host health, performance, and ultimately on fitness. Disease resistance is the host trait that prevents infection or reduces the number of pathogens, parasites and herbivores within or on a host. In some embodiments, tolerant plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. Additionally, the level of field inoculum and temperature are the two main factors effecting symptom expression of a lettuce plant for tolerance.

Another embodiment comprises at least 1, 2, 3, 4, 5, 6, 7, 8, 9, 10 or more of the morphological and physiological characteristics of lettuce variety Teton (e.g., as described in Table 1).

Another embodiment also encompasses plant parts, plant material, pollen, ovules, leaves, fruit and seed from the lettuce plants of Teton. Also provided is a tissue culture of regenerable cells from the lettuce plants of Teton, where optionally, the regenerable cells are: (a) embryos, embryo sac, microspore, cutting (rooted or unrooted), ovary, protoplast, meristem, leaves, cell, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are lettuce plants regenerated from a tissue culture of Teton. Further embodiments provide for propagation material for producing plants of lettuce variety Teton. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. Further embodiments to propagation material which may comprise parts of the plant that are suitable for vegetative reproduction, for example cuttings, roots, stems, cells, protoplasts.

Another embodiment provides for a method of determining a genetic characteristic of lettuce variety Teton or a progeny thereof, e.g., a method of determining a genotype of lettuce variety Teton or a progeny thereof. In embodiments, the method comprises detecting in the genome of a Teton plant, or a progeny plant thereof, at least a first polymorphism. To illustrate, in embodiments, the method comprises obtaining a sample of nucleic acids from the plant and detecting at least a first polymorphism in the nucleic acid sample (e.g., using one or more molecular markers). Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. Another embodiment further provides for a computer readable medium produced by such a method.

In addition to the exemplary aspects and embodiments described above, further aspects and embodiments will become apparent by study of the following descriptions.

DETAILED DESCRIPTION

Lettuce variety Teton is a romaine lettuce variety with resistance to Lettuce Necrotic Stunt Virus, Corky Root (*Rhizomonas suberifaciens*), with moderate resistance to *Sclerotinia*. Teton has been shown to also have moderate resistance to tip burn. Teton has shown no variants other than what would normally be expected due to the environment.

TABLE 1

| VARIETY DESCRIPTION INFORMATION |
|---|
| Plant type: Romaine |
| Seed: |
| Color: Tan |
| Light dormancy: Absent |
| Heat dormancy: Present |

TABLE 1-continued

VARIETY DESCRIPTION INFORMATION

Mature leaves:

Incision depth: Not applicable
Margin, indentation: Absent
Margin, undulations of the apical margin: Very slight
Hue of green color of outer leaves: Not applicable
Intensity of color of outer leaves: Not applicable
Anthocyanin distribution: Not applicable
Glossiness: Slight
Blistering: Slight
Leaf thickness: Thick
Trichomes: Absent
Plant:

Maturity date: 72 days
Planting: Apr. 29, 2020
Harvest: Jul. 10, 2020
Frame: 13.0 inches to 14.5 inches
Head diameter: Not applicable
Head shape: Spatulate
Head size class: Large
Head weight: 450 g to 770 g
Head firmness: Moderate density
Height: 13.0 inches to 15.0 inches
Butt:

Shape: V-shaped
Midrib: Moderately protruding
Core:

Diameter: 4.0 cm to 5.0 cm
Core height: 2.25 cm to 3.25 cm
Bolting:

First water date: Apr. 17, 2020
Number of days from first water date to seed stalk emergence
(summer conditions): 63
Time to beginning of bolting: Jun. 20, 2020
Bolting class: Moderate
Bolt height: 36.0 inches to 41.0 inches
Spread of frame: 17.0 inches to 18.0 inches
Bolter leaf margin: Smooth
Bolter leaf color: RHS 136A
Bolter habit:
Terminal inflorescence: Present
Lateral shoots: Present
Basal side shoots: Absent
Disease/Insect resistance/Physiological Stress:
Disease:

Lettuce Mosaic Virus: Not tested
Downy Mildew (*Bremia lactucae*): Not tested
Lettuce Necrotic Stunt Virus: Resistant by field screens
Corky Root (*Rhizomonas suberifaciens*): Resistant by descent
Sclerotinia: Moderately resistant by field screens
Pests

*Nasonovia ribisnigri*: Susceptible to Nr0 and Nr1
Physiological stresses:

Tip burn: Moderately resistant

Table 2 shows an explanation of selected disease/insect/ and physiological stresses.

TABLE 2

Explanation of Disease/Insect resistance/Physiological Stresses

| | |
|---|---|
| Big Vein | A disease of lettuce caused by Lettuce Mirafiori Big Vein Virus which is transmitted by the fungus *Olpidium virulentus*, with vein clearing and leaf shrinkage resulting in plants of poor quality and reduced marketable value. |

TABLE 2-continued

Explanation of Disease/Insect resistance/Physiological Stresses

| | |
|---|---|
| Lettuce Mosaic | A disease that can cause a stunted, deformed, or mottled pattern in young lettuce and yellow, twisted, and deformed leaves in older lettuce. |
| Downy Mildew | A fungal disease caused by an Oomycete that causes downy mildew in lettuce in cooler growing regions. |
| Verticillium Wilt | A fungal disease caused by *Verticillium dahlia*. Initial symptoms of Verticillium wilt appear at the rosette stage when the lower leaves wilt. As an infected plant develops, the outer whorl of leaves turns yellow, wilts, and dies. Those leaves closest to the lettuce head can yellow, die, and remain closely appressed (attached) to the head. |
| Tip burn | Means a browning of the edges or tips of lettuce leaves that is a physiological response to a lack of calcium. |
| Fusarium Wilt | A disease caused by the fungus *Fusarium oxysporum f.* sp. *Lactucum*. Fusarium wilt causes infected seedlings to wilt and possibly die. Inner tissues of affected seedlings are red or brown. In older plants, leaves turn yellow and develop tip burn. Internally, the vascular system is brown to black in the leaves, and a reddish-brown discoloration develops in the cortex of the crown and upper root. Plants may be stunted and fail to form heads. |

Table 3 below provides a comparison of the Teton variety with the commercial variety Vanguard PIC. The varieties were grown near King City, California with a plant date of Apr. 16, 2021. An in-field evaluation of the two varieties was conducted on Jun. 24, 2021 of whole head weight (grams), plant height (cm), core length (cm), tipburn (present/absent).

Table 4 below provides a second comparison of the Teton variety post harvest with the commercial variety Vanguard PIC. The varieties were grown near King City, California with a plant date of Apr. 16, 2021. A harvest evaluation was conducted on Jun. 28, 2021 of whole head weight (grams), plant height (cm), core length (cm), tipburn (present/absent.

TABLE 3

The varieties were grown near King City, California with a plant date of Apr. 16, 2021. An in-field evaluation of the two varieties was conducted on Jun. 24, 2021

| Whole Head Weight (grams) | | Plant Height (cm) | | Core Length (cm) | | Tipburn (present (Yes)/absent (N)) | |
|---|---|---|---|---|---|---|---|
| Vanguard PIC | Teton | Vanguard PIC | Teton | Vanguard PIC | Teton | Vanguard PIC | Teton |
| 855 | 926 | 29 | 32 | 3 | 5.5 | NO | NO |
| 970 | 991 | 30 | 34 | 6 | 5 | NO | YES |
| 830 | 667 | 29 | 32 | 4 | 3 | NO | NO |
| 768 | 720 | 31 | 30 | 5.5 | 5 | NO | NO |
| 980 | 730 | 31 | 29 | 6.5 | 4 | NO | NO |
| 613 | 732 | 27 | 32 | 3.5 | 4.5 | NO | NO |
| 884 | 817 | 30 | 33 | 4.5 | 6 | NO | NO |
| 931 | 930 | 28 | 31 | 6 | 5 | NO | NO |
| 936 | 966 | 32 | 36 | 5.5 | 7 | NO | NO |
| 997 | 724 | 30 | 31 | 6 | 5 | NO | NO |
| 1105 | 770 | 32 | 30 | 7 | 5 | NO | NO |
| 886 | 818 | 30 | 30 | 6.5 | 5 | NO | NO |
| 851 | 721 | 31 | 31 | 6.5 | 5.5 | NO | YES |
| 694 | 934 | 32 | 30 | 5.5 | 3 | NO | NO |
| 985 | 886 | 31 | 31 | 6 | 4 | NO | NO |
| 935 | 834 | 30 | 33 | 6 | 6.5 | NO | NO |
| 752 | 587 | 28 | 33 | 5 | 5.5 | NO | NO |
| 854 | 1015 | 28 | 29 | 6.5 | 6.5 | NO | YES |

TABLE 4

The varieties were grown near King City, California with a plant date of Apr. 16, 2021. A post-harvest evaluation of the two varieties was conducted on Jun. 28, 2021

| Whole Head Weight (grams) | | Plant Height (cm) | | Core Length (cm) | | Tipburn (present(Yes)/ absent(No)) | |
|---|---|---|---|---|---|---|---|
| Vanguard PIC | Teton | Vanguard PIC | Teton | Vanguard PIC | Teton | Vanguard PIC | Teton |
| 789 | 784 | 30 | 32 | 5 | 6 | NO | NO |
| 859 | 848 | 29 | 33 | 4 | 6 | NO | YES |
| 672 | 762 | 29 | 34 | 7 | 6 | NO | YES |
| 808 | 972 | 32 | 36 | 7.5 | 6 | NO | YES |
| 784 | 1014 | 28 | 35 | 5 | 6.5 | NO | NO |
| 688 | 745 | 32 | 31 | 6 | 6 | NO | NO |
| 900 | 806 | 33 | 33 | 8 | 7 | NO | YES |
| 895 | 692 | 33 | 33 | 6 | 5 | NO | NO |

Further Embodiments

Breeding with Lettuce Variety Teton

The complexity of inheritance influences choice of the breeding method. Backcross breeding is used to transfer one or a few favorable genes for a highly heritable trait into a desirable variety. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Promising advanced breeding lines are thoroughly tested and compared to appropriate standards in environments representative of the commercial target area(s) for three or more years. The best lines are candidates for new commercial varieties; those still deficient in a few traits may be used as parents to produce new populations for further selection.

These processes, which lead to the final step of marketing and distribution, is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard variety. If a single observation is inconclusive, replicated observations provide a better estimate of its genetic worth.

The goal of lettuce breeding is to develop new and superior lettuce varieties and hybrids. The breeder initially selects and crosses two or more parental lines, followed by repeated selfing and selection, producing many new genetic combinations. The breeder can theoretically generate billions of different genetic combinations via crossing, selection, selfing and mutations.

Using Lettuce Variety Teton to Develop Other Lettuce Varieties

Lettuce varieties such as lettuce variety Teton are typically developed for fresh consumption. However, lettuce varieties such as lettuce variety Teton also provide a source of breeding material that may be used to develop new lettuce varieties. Plant breeding techniques known in the art and used in a lettuce breeding program include, but are not limited to, recurrent selection, bulk selection, mass selection, backcrossing, pedigree breeding, open pollination breeding, restriction fragment length polymorphism enhanced selection, genetic marker enhanced selection, making double haploids, transformation, and gene editing. These techniques can be used singularly or in combinations. The development of lettuce varieties in a breeding program requires, in general, the development and evaluation of homozygous varieties. There are many analytical methods available to evaluate a new variety. The oldest and most traditional method of analysis is the observation of phenotypic traits, but genotypic analysis may also be used.

Additional Breeding Methods

One embodiment is directed to methods for producing a lettuce plant by crossing a first parent lettuce plant with a second parent lettuce plant, wherein the first or second lettuce plant is the lettuce plant from lettuce variety Teton. Further, both first and second parent lettuce plants may be from lettuce variety Teton. Any plants produced using lettuce variety Teton as at least one parent are also within the scope of the embodiments. These methods are well known in the art and some of the more commonly used breeding methods are described herein. Descriptions of breeding methods can be found in one of several reference books (e.g., Allard, *Principles of Plant Breeding* (1960); Simmonds, *Principles of Crop Improvement* (1979); Sneep, et al. (1979); Cooper, S. G., D. S. Douches and E. J. Grafius. (2004).

The following describes breeding methods that may be used with lettuce variety Teton in the development of further lettuce plants. One such embodiment is a method for developing a lettuce variety Teton progeny plant in a lettuce breeding program comprising: obtaining the lettuce plant, or a part thereof, of lettuce variety Teton, utilizing said plant, or plant part, as a source of breeding material, and selecting a lettuce variety Teton progeny plant with molecular markers in common with lettuce variety Teton and/or with morphological and/or physiological characteristics selected from the characteristics listed in Table 1. Breeding steps that may be used in the lettuce plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of lettuce variety Teton progeny lettuce plants, comprising crossing lettuce variety Teton with another lettuce plant, thereby producing a population of lettuce plants which derive 50% of their alleles from lettuce variety Teton. A plant of this population may be selected and repeatedly selfed or sibbed with a lettuce line resulting from these successive filial generations. One embodiment is the hybrid lettuce produced by this method and that has obtained at least 50% of its alleles from lettuce variety Teton.

One of ordinary skill in the art of plant breeding would know how to evaluate the traits of two plant varieties to determine if there is no significant difference between the two traits expressed by those varieties. For example, see, Fehr and Walt, *Principles of Variety Development*, pp. 261-286 (1987). Thus, embodiments include lettuce variety Teton progeny lettuce plants comprising a combination of at least two lettuce variety Teton traits selected from the group consisting of those listed in Table 1 and a combination of traits listed in the Summary, so that said progeny lettuce plant is not significantly different for said traits than lettuce variety Teton as determined at the 5% significance level when grown in the same environmental conditions. Using techniques described herein, molecular markers may be used to identify said progeny plant as a lettuce variety Teton progeny plant. Mean trait values may be used to determine whether trait differences are significant, and the traits may be measured on plants grown under the same environmental conditions. Once such a variety is developed, its value is substantial since it is important to advance the germplasm base as a whole in order to maintain or improve traits such as yield, disease tolerance, pest tolerance, and plant performance in extreme environmental conditions.

Progeny of lettuce variety Teton may also be characterized through their filial relationship with lettuce variety Teton, as for example, being within a certain number of breeding crosses of lettuce variety Teton. A breeding cross is a cross made to introduce new genetics into the progeny, and is distinguished from a self or a sib cross, which is made to select among existing genetic alleles. The lower the number of breeding crosses in the pedigree, the closer the relationship between lettuce variety Teton and its progeny. For example, progeny produced by the methods described herein may be within 1, 2, 3, 4, or 5 breeding crosses of lettuce variety Teton.

Pedigree Breeding

Pedigree breeding starts with the crossing of two genotypes, such as lettuce variety Teton and another lettuce plant having one or more desirable characteristics that is lacking or which complements lettuce variety Teton. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically, in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety.

Backcross Breeding

Backcross breeding has been used to transfer genes for a simply inherited, highly heritable trait into a desirable homozygous variety or hybrid which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent (e.g., variety) and the desirable trait transferred from the donor parent. This is also known as single gene conversion and/or backcross conversion.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. It may be necessary to introduce a test of the progeny to determine if the desired characteristic has been successfully transferred.

A backcross conversion of lettuce variety Teton occurs when DNA sequences are introduced through backcrossing, with lettuce variety Teton utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Frisch M. et al, "Marker-Assisted Backcrossing for Simultaneous Introgression of Two Genes" *Crop Science Society of America*, pp 1716-1725 (2001) and Openshaw, S. J., et al., "Marker-assisted Selection in Backcross Breeding, Proceedings Symposium of the Analysis of Molecular Data" *Crop Science Society of America*, Corvallis, Oreg. (August 1994), where it was demonstrated that a backcross conversion could be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. Desired traits that may be transferred through backcross conversion include, but are not limited to, sterility (nuclear and cytoplasmic), fertility restoration, nutritional enhancements, drought tolerance, nitrogen utilization, low phytate, industrial enhancements, disease tolerance (bacterial, fungal, or viral), insect tolerance, and herbicide tolerance. In addition, an introgression site itself, such as an FRT site, Lox site, or other site-specific integration site, may be inserted by backcrossing and utilized for direct insertion of one or more genes of interest into a specific plant variety. In some embodiments, the number of loci that may be backcrossed into lettuce variety Teton is at least 1, 2, 3, 4, or 5, and/or no more than 6, 5, 4, 3, or 2. A single locus may contain several transgenes, such as a transgene for disease tolerance that, in the same expression vector, also contains a transgene for herbicide tolerance. The gene for herbicide tolerance may be used as a selectable marker and/or as a phenotypic trait. A single locus conversion of site-specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing each backcross generation to determine which plants carry the recessive alleles unless molecular markers are available to track the gene. Recessive traits may require additional progeny testing in successive backcross generations to confirm the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. The backcross is a form of inbreeding, and the features of the recurrent parent are automatically recovered after successive backcrosses. Poehlman, "*Breeding Field Crops*" p. 204 (1987). Poehlman suggests from one to four or more backcrosses, but as noted above, the number of backcrosses necessary can be reduced with the use of molecular markers. Other factors, such as a genetically similar donor parent, may also reduce the number of backcrosses necessary. As noted by Poehlman, backcrossing is easiest for simply inherited, dominant, and easily recognized traits.

One process for adding or modifying a trait or locus in lettuce variety Teton comprises crossing lettuce variety Teton plants grown from lettuce variety Teton seed with plants of another lettuce plant that comprises the desired trait or locus, selecting $F_1$ progeny plants that comprise the desired trait or locus to produce selected $F_1$ progeny plants, crossing the selected progeny plants with the lettuce variety Teton plants to produce backcross progeny plants, selecting for backcross progeny plants that have the desired trait or locus and the morphological characteristics of lettuce variety Teton to produce selected backcross progeny plants, and backcrossing to lettuce variety Teton three or more times in succession to produce selected fourth or higher backcross progeny plants that comprise said trait or locus. The modified lettuce variety Teton may be further characterized as having the physiological and morphological characteristics of lettuce variety Teton listed in Table 1 as determined at the 5% significance level when grown in the same environmental conditions and/or may be characterized by percent similarity or identity to lettuce variety Teton as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox, and other sites for site specific integration, which may also affect a desired trait if a functional nucleic acid is inserted at the integration site.

In addition, the above process and other similar processes described herein may be used to produce first generation progeny lettuce seed by adding a step at the end of the process that comprises crossing lettuce variety Teton with the introgressed trait or locus with a different lettuce plant and harvesting the resultant first generation progeny lettuce seed.

Many single gene traits have been identified that are not regularly selected for in the development of a new variety but that can be improved by backcrossing techniques well-known in the art. Single gene traits may or may not be transgenic. Examples of these traits include, but are not limited to, herbicide tolerance, insect tolerance, tolerance for bacterial, fungal, or viral disease, male fertility, male sterility, enhanced nutritional quality, modified carbohydrate metabolism, modified yield, environmental stress tolerance, and industrial usage In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, lettuce variety Teton may be crossed with another variety to produce a first-generation progeny plant. The first-generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new lettuce varieties.

Therefore, an embodiment of the present disclosure is a method of making a backcross conversion lettuce variety Teton, comprising the steps of crossing a plant of lettuce variety Teton with a donor plant comprising a desired trait, selecting an $F_1$ progeny plant comprising the desired trait, and backcrossing the selected $F_1$ progeny plant to a plant of lettuce variety Teton to produce $BC_1$, $BC_2$, $BC_3$, etc. This method may further comprise the step of obtaining a molecular marker profile of lettuce variety Teton and using the molecular marker profile to select for a progeny plant with the desired trait and the molecular marker profile of lettuce variety Teton. In one embodiment, the desired trait is a mutant gene, gene, or transgene present in the donor parent.

Recurrent Selection and Mass Selection

Recurrent selection is a method used in a plant breeding program to improve a population of plants. Lettuce variety Teton is suitable for use in a recurrent selection program. The method entails individual plants cross pollinating with each other to form progeny. The progeny are grown and the superior progeny selected by any number of selection methods, which include individual plant, half-sib progeny, full-sib progeny, and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating crops. A genetically variable population of heterozygous individuals is either identified, or created, by intercrossing several different parents. The plants are selected based on individual superiority, outstanding progeny, or excellent combining ability. The selected plants are intercrossed to produce a new population in which further cycles of selection are continued.

Mutation Breeding

Mutation breeding is another method of introducing new traits into lettuce variety Teton. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions (also known as somaclonal variation), radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (about from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Fehr, "Principles of Variety Development," *Macmillan Publishing Company* (1993). In addition, mutations created in other lettuce plants may be used to produce a backcross conversion of lettuce variety Teton that comprises such mutation.

Additional methods include, but are not limited to, expression vectors introduced into plant tissues using a direct gene transfer method, such as microprojectile-mediated delivery, DNA injection, electroporation, and the like. The expression vectors may be introduced into plant tissues by using either microprojectile-mediated delivery with a biolistic device or by using *Agrobacterium*-mediated transformation. Transformant plants obtained with the protoplasm of the embodiments are intended to be within the scope of the embodiments.

Gene Editing Using CRISPR

Targeted gene editing can be done using CRISPR/Cas9 technology (Saunders & Joung, *Nature Biotechnology*, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system, including *Capsicum annuum*. See for example, Lien D. Bertier, et al., High-Resolution Analysis of the Efficiency, Heritability, and Editing Outcomes of CRISPR/Cas9-Induced Modifications of NCED4 in Lettuce (*Lactuca sativa*). *G3: GENES, GENOMES, GENETICS* May 1, 2018 vol. 8 no. 5 1513-1521; U.S. Application Publication No. WO2014068346 (Gyorgy et al., Identification of a *Xanthomonas euvesicatoria* resistance gene from pepper (*Capsicum annuum*) and method for generating plants with resistance), Martinelli, F. et al., "Proposal of a Genome Editing System for Genetic Resistance to Tomato Spotted Wilt Virus" *American Journal of Applied Sciences* 2014, and Noman, A. et al., "CRISPR-Cas9: Tool for Qualitative and Quantitative Plant Genome Editing" *Frontiers in Plant Science* Vol. 7 Nov. 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476. Therefore, it is another embodiment to use the CRISPR system on lettuce variety Teton to modify traits and tolerances to pests, herbicides, and viruses.

Introduction of a New Trait or Locus into Lettuce Variety Teton

Lettuce variety Teton represents a new variety into which a new locus or trait may be introgressed. Direct transformation and backcrossing represent two important methods that can be used to accomplish such an introgression. The term backcross conversion and single locus conversion are used interchangeably to designate the product of a backcrossing program.

Molecular Techniques Using Lettuce Variety Teton

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to "alter" (the utilization of up-regulation, down-regulation, or gene silencing) the traits of a plant in a specific manner. Any DNA sequences, whether from a different species or from the same species, which are introduced into the genome using transformation or various breeding methods are referred to herein collectively as "transgenes." In some embodiments, a transgenic variant of lettuce variety Teton may contain at least one transgene. Over the last fifteen to twenty years several methods for producing transgenic plants have been developed, and another embodiment also relates to transgenic variants of the claimed lettuce variety Teton.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the embodiments may be produced by any means, including genomic preparations, cDNA preparations, in-vitro synthesis, RT-PCR, and in vitro or in vivo transcription.

One embodiment is a process for producing lettuce variety Teton further comprising a desired trait, said process comprising introducing a transgene that confers a desired trait to a lettuce plant of lettuce variety Teton. Another embodiment is the product produced by this process. In one embodiment, the desired trait may be one or more of herbicide tolerance, insect tolerance, disease tolerance, environmental stress tolerance, or modified carbohydrate metabolism. The specific gene may be any known in the art or listed herein, including: a polynucleotide conferring resistance to imidazolinone, dicamba, sulfonylurea, glyphosate, glufosinate, triazine, PPO-inhibitor herbicides, benzonitrile, cyclohexanedione, phenoxy proprionic acid, and L-phosphinothricin; a polynucleotide encoding a *Bacillus thuringiensis* polypeptide; or a polynucleotide conferring resistance to Tomato spotted wilt virus, *Xanthomonas euvesicatoria*, Bs2, CARAV1, or CaPMEI1.

Numerous methods for plant transformation have been developed, including biological and physical plant transformation protocols. See, for example, Pileggi, Marcos, et al, An Improved Method for Transformation of Lettuce by *Agrobacterium tumefaciens* with a Gene that Confers Freezing Resistance. *Brazilian Archives of Biology and Technology*. Vol. 44(2): pp. 191-196, June, 2001; Michelmore, Al, et al., Transformation of lettuce (*Lactuca sativa*) mediated by *Agrobacterium tumefaciens*. Plant Cell Rep. 1987 December; 6(6):439-42; Li D. et al, "Establishment of a highly efficient transformation system for pepper (*Capsicum annuum* L.)" *Plant Cell Reports*, pp 785-788 (2003), and Lee Y. H. et al, "A new selection method for pepper transformation: callus-mediated shoot formation" *Plant Cell Reports* pp 50-58 (2004). In addition, expression vectors and in vitro culture methods for plant cell or tissue transformation and regeneration of plants are available. See, for example, Gruber, et al., "Vectors for Plant Transformation," in *Methods in Plant Molecular Biology and Biotechnology*, Glick and Thompson Eds., CRC Press, Inc., Boca Raton, pp. 89-119 (1993) and Nakagawa T. et al, "Development of series of gateway binary vectors, pGWBs, for realizing efficient construction of fusion genes for plant transformation" *Journal of Bioscience and Bioengineering* pp 34-41 (2007).

A genetic trait which has been engineered into the genome of a particular lettuce plant may then be moved into the genome of another variety using traditional breeding techniques that are well known in the plant breeding arts. For example, a backcrossing approach is commonly used to move a transgene from a transformed lettuce line into an already lettuce line, and the resulting backcross conversion plant would then comprise the transgene(s).

Various genetic elements can be introduced into the plant genome using transformation. These elements include, but are not limited to, genes, coding sequences, inducible, constitutive and tissue specific promoters, enhancing sequences, and signal and targeting sequences. For example, see the traits, genes, and transformation methods listed in U.S. Pat. No. 6,118,055.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Amplified Fragment Length Polymorphisms (AFLPs), Arbitrarily Primed Polymerase Chain Reaction (AP-PCR), DNA Amplification Fingerprinting (DAF), Sequence Characterized Amplified Regions (SCARs), Simple Sequence Repeats (SSRs), and Single Nucleotide Polymorphisms (SNPs) may be used in plant breeding methods utilizing lettuce variety Teton.

Isozyme Electrophoresis and RFLPs have been widely used to determine genetic composition. See for example, Kesseli, R. V., et al., Analysis of a detailed genetic linkage map of *Lactuca sativa* (lettuce) constructed from RFLP and RAPD markers. Genetics. 1994 April; 136(4):1435-46.

Randomly Amplified Polymorphic DNAs (RAPDs) and Amplified Fragment Length Polymorphisms (AFLPs) may also be used. See for example, Sharma, S. et al., Assessment of genetic diversity in lettuce (*Lactuca sativa* L.) germplasm using RAPD markers. 3 *Biotech*. 2018 January; 8(1):9.

SSR technology can be routinely used. See for example, Rauscher, G. et al., Development of genomic SSR markers for fingerprinting lettuce (*Lactuca sativa* L.) cultivars and mapping genes. *BMC Plant Biology*. 13:11 (2013).

Single Nucleotide Polymorphisms (SNPs) may also be used to identify the unique genetic composition of the embodiment(s) and progeny varieties retaining that unique genetic composition. See for example, Simko, I., et al., Association mapping and marker-assisted selection of the lettuce dieback resistance gene Tvr1. *BMC Plant Biol*. 9: 135 (2009) and Simko, I., et al., Molecular markers reliably predict post-harvest deterioration of fresh-cut lettuce in modified atmosphere packaging. *Horticulture Research*. Volume 5, Article number: 21 (2018)

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome. See for example, Hartman, et al., Abiotic stress QTL in lettuce crop-wild hybrids: comparing greenhouse and field experiments. *Ecol Evol*. 2014 June; 4(12): 2395-2409. QTL markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a lettuce plant for which lettuce variety Teton is a parent can be used to produce double haploid plants. Double haploids are produced by the doubling of a set of chromosomes (1N) from a heterozygous plant to produce a completely homozygous individual. This can be advantageous because the process omits the generations of selfing needed to obtain a homozygous plant from a heterozygous source. For example, see, Piosik, L., Haploid embryos of lettuce (*Lactuca sativa*) induced by alien pollen or chemical factors. *African Journal of Biotechnology*. Vol. 12(4), pp. 345-352, 23 Jan. 2013.

Thus, an embodiment is a process for making a substantially homozygous lettuce variety Teton progeny plant by producing or obtaining a seed from the cross of lettuce variety Teton and another lettuce plant and applying double haploid methods to the $F_1$ seed or $F_1$ plant or to any successive filial generation.

In particular, a process of making seed retaining the molecular marker profile of lettuce variety Teton is contemplated, such process comprising obtaining or producing $F_1$ seed for which lettuce variety Teton is a parent, inducing doubled haploids to create progeny without the occurrence of meiotic segregation, obtaining the molecular marker profile of lettuce variety Teton, and selecting progeny that retain the molecular marker profile of lettuce variety Teton.

Expression Vectors for Lettuce Transformation: Marker Genes

Plant transformation involves the construction of an expression vector which will function in plant cells. Such a vector comprises DNA comprising a gene under control of, or operatively linked to, a regulatory element (for example, a promoter). Expression vectors include at least one genetic marker operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well-known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene which, when under the control of plant regulatory signals, confers resistance to kanamycin. Another commonly used selectable marker gene is the hygromycin phosphotransferase gene which confers resistance to the antibiotic hygromycin.

Additional selectable marker genes include Pain1-9a and Pain1-8c which both correspond to the group a alleles of the vacuolar acid invertase gene; Pain1prom-d/e; Stp23-8b, StpL-3b, and StpL-3e which originate from two plastid starch phosphorylase genes; AGPsS-9a which is positively associated an increase in plant starch content, starch yield and chip quality, and AGPsS-10a which is associated with a decrease in the average plant starch content, starch yield and chip quality; GP171-a which corresponds to allele 1a of ribulose bisphosphate carboxylase activase; and Rca-1a.

Selectable marker genes for plant transformation not of bacterial origin include, for example, mouse dihydrofolate reductase, plant 5-enolpyruvylshikimate-3-phosphate synthase, and plant acetolactate synthase (Eichholtz, et al., *Somatic Cell Mol. Genet.*, 13:67 (1987); Shah, et al., *Science*, 233:478 (1986); Charest, et al., *Plant Cell Rep.*, 8:643 (1990)).

Another class of marker genes for plant transformation requires screening of presumptively transformed plant cells, rather than direct genetic selection of transformed cells, for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used marker genes for screening presumptively transformed cells include β-glucuronidase (GUS), β-galactosidase, luciferase, and chloramphenicol acetyltransferase (Jefferson, R. A., *Plant Mol. Biol. Rep.*, 5:387 (1987); Teeri, et al., *EMBO J.*, 8:343 (1989); Koncz, et al., *Proc. Natl. Acad. Sci. USA*, 84:131 (1987); DeBlock, et al., *EMBO J.*, 3:1681 (1984)).

Expression Vectors for Lettuce Transformation: Promoters

Genes included in expression vectors must be driven by a nucleotide sequence comprising a regulatory element (for example, a promoter). Several types of promoters are well known in the transformation arts as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in a certain tissue are referred to as "tissue-specific." A "cell-type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell-type specific, and inducible promoters constitute the class of "non-constitutive" promoters. A "constitutive" promoter is a promoter that is active under most environmental conditions. Many types of promoters are well known in the art.

Signal Sequences for Targeting Proteins to Subcellular Compartments

Transport of a protein produced by transgenes to a subcellular compartment, such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine during protein synthesis and processing where the encoded protein is ultimately compartmentalized. Many signal sequences are well-known in the art. See, for example, Becker, et al., *Plant Mol. Biol.*, 20:49 (1992); Knox, C., et al., *Plant Mol. Biol.*, 9:3-17 (1987); Lerner, et al., *Plant Physiol.*, 91:124-129 (1989); Frontes, et al., *Plant Cell*, 3:483-496 (1991); Matsuoka, et al., *Proc. Natl. Acad. Sci.*, 88:834 (1991); Gould, et al., *J Cell. Biol.*, 108:1657 (1989); Creissen, et al., *Plant J.*, 2:129 (1991); Kalderon, et al., *Cell*, 39:499-509 (1984); Steifel, et al., *Plant Cell*, 2:785-793 (1990).

Foreign Protein Genes and Agronomic Genes: Transformation

With transgenic plants, according to one embodiment, a foreign protein can be produced in commercial quantities. Thus, techniques for the selection and propagation of transformed plants, which are well understood in the art, yield a plurality of transgenic plants which are harvested in a conventional manner, and a foreign protein can then be extracted from a tissue of interest or from total biomass. Protein extraction from plant biomass can be accomplished by known methods which are discussed, for example, by Heney and Orr, *Anal. Biochem.*, 114:92-6 (1981).

According to an embodiment, the transgenic plant provided for commercial production of foreign protein is a lettuce plant. In another embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see, Glick and Thompson, *Methods in Plant Molecular Biology and Biotechnology*, CRC Press, Inc., Boca Raton, 269:284 (1993). Map information concerning chromosomal location is useful for proprietary protection of a subject transgenic plant.

Likewise, by means of one embodiment, plants can be genetically engineered to express various phenotypes of agronomic interest. Through the transformation of lettuce, the expression of genes can be altered to enhance disease tolerance, insect tolerance, herbicide tolerance, agronomic, grain quality, and other traits. Transformation can also be used to insert DNA sequences which control or help control male-sterility. DNA sequences native to lettuce, as well as non-native DNA sequences, can be transformed into lettuce and used to alter levels of native or non-native proteins. Various promoters, targeting sequences, enhancing sequences, and other DNA sequences can be inserted into the genome for the purpose of altering the expression of proteins. The interruption or suppression of the expression of a gene at the level of transcription or translation (also known as gene silencing or gene suppression) is desirable for several aspects of genetic engineering in plants.

Many techniques for altering gene are well-known to one of skill in the art, including, but not limited to, knock-outs (such as by insertion of a transposable element such as Mu (Vicki Chandler, *The Maize Handbook*, Ch. 118 (Springer-Verlag 1994)) or other genetic elements such as a FRT, Lox, or other site specific integration sites; antisense technology (see, e.g., Sheehy, et al., *PNAS USA*, 85:8805-8809 (1988) and U.S. Pat. Nos. 5,107,065, 5,453,566, and 5,759,829); co-suppression (e.g., Taylor, *Plant Cell*, 9:1245 (1997); Jorgensen, *Trends Biotech.*, 8(12):340-344 (1990); Flavell, *PNAS USA*, 91:3490-3496 (1994); Finnegan, et al., *Bio/Technology*, 12:883-888 (1994); Neuhuber, et al., *Mol. Gen. Genet.*, 244:230-241 (1994)); RNA interference (Napoli, et al., *Plant Cell*, 2:279-289 (1990); U.S. Pat. No. 5,034,323; Sharp, *Genes Dev.*, 13:139-141 (1999); Zamore, et al., *Cell*, 101:25-33 (2000); Montgomery, et al., *PNAS USA*, 95:15502-15507 (1998)), virus-induced gene silencing (Burton, et al., *Plant Cell*, 12:691-705 (2000); Baulcombe, *Curr. Op. Plant Bio.*, 2:109-113 (1999)); target-RNA-specific ribozymes (Haseloff, et al., *Nature*, 334:585-591 (1988)); hairpin structures (Smith, et al., *Nature*, 407:319-320 (2000); U.S. Pat. Nos. 6,423,885, 7,138,565, 6,753,139, and 7,713,715); MicroRNA (Aukerman & Sakai, *Plant Cell*, 15:2730-2741 (2003)); ribozymes (Steinecke, et al., *EMBO J.*, 11:1525 (1992); Perriman, et al., *Antisense Res. Dev.*, 3:253 (1993)); oligonucleotide mediated targeted modification (e.g., U.S. Pat. Nos. 6,528,700 and 6,911,575); Zn-finger targeted molecules (e.g., U.S. Pat. Nos. 7,151,201, 6,453,242, 6,785,613, 7,177,766 and 7,788,044); and other methods or combinations of the above methods known to those of skill in the art.

The foregoing methods for transformation may be used for producing a transgenic variety. The transgenic variety could then be crossed with another (non-transformed or transformed) variety in order to produce a new transgenic variety. Alternatively, a genetic trait that has been engineered into a particular lettuce variety using the foregoing transformation techniques could be moved into another line using traditional backcrossing techniques that are well known in the plant breeding arts. For example, a backcrossing approach could be used to move an engineered trait from a public, non-elite variety into an elite variety, or from a variety containing a foreign gene in its genome into a variety or varieties that do not contain that gene. As used herein, "crossing" can refer to a simple x by y cross or the process of backcrossing depending on the context.

Likewise, by means of one embodiment, agronomic genes can be expressed in transformed plants. More particularly, plants can be genetically engineered to express various phenotypes of agronomic interest, including, but not limited to, genes that confer resistance to pests or disease, genes that confer resistance to an herbicide, genes that confer or contribute to a value-added or desired trait, genes that control male sterility, genes that create a site for site specific DNA integration, and genes that affect abiotic stress resistance. Many hundreds if not thousands of different genes are known and could potentially be introduced into a lettuce plant according to one or more embodiments. Non-limiting examples of particular genes and corresponding phenotypes one may choose to introduce into a lettuce plant include one or more genes for insect tolerance, such as a in *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety. Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of one or more embodiments.

Tissue Culture

Further reproduction of the variety can occur by tissue culture and regeneration. Tissue culture of various tissues of lettuce and regeneration of plants therefrom is well-known and widely published. See, Agrawal, S. et al., "Plant regeneration in tissue cultures of pepper (*Capsicum annuum* L. cv.

Mathania) *Plant Cell, Tissue and Organ Culture*, Vol. 16(1) pp 47-55 1989; Berljak J. "In vitro plant regeneration from Pepper (*Capsicum annuum* L. cv. 'Soroksari') Seedling Explants" *Phyton (Austria) Special issue: "Plant Physiology"* Vol. 39(3) pp 289-292 (1999); Ahmad, N., et al., "Improved plant regeneration in *Capsicum annuum* L. from nodal segments" *Biologia Plantarum* Vol. 50(4) pp 701-704 (2006); and Otroshy, M. et al., "Micropropagation of Pepper (*Capsicum annuum* L.) Through in vitro Direct Organogenesis" *Asian Journal of Biotechnology* Vol. 3 pp 38-45 (2010). Thus, another aspect or embodiment is to provide cells which upon growth and differentiation produce lettuce plants having the physiological and morphological characteristics of lettuce variety Teton.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, petioles, leaves, stems, roots, root tips, anthers, pistils, ovules, protoplasts, meristematic cells, callus, leaves, cotyledons, hypocotyl, roots, root tips, flowers, seeds, petiole, microspore, leaf, ovary, embryo sac, cutting, protoplast, or a cell, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference. Another embodiment relates to tissue culture produced from protoplasts or cells from the lettuce plants disclosed in the subject application, wherein said cells or protoplasts are produced from a plant part selected from the group consisting of pollen, ovules, embryos, protoplasts, meristematic cells, callus, pollen, leaves, ovules, anthers, cotyledons, hypocotyl, pistils, roots, root tips, flowers, seeds, petiole, microspore, leaf, ovary, embryo sac, embryo, cutting, stem, protoplast, anther, or a cell.

Another embodiment relates to a plant, or a part thereof, produced by growing lettuce variety Teton, wherein the plant part comprises at least one cell of lettuce variety Teton.

Industrial Uses

Lettuce has a wide variety of uses in the commodity area. For example, fresh lettuce can be used to make chopped and prepared salads. Thus, a further embodiment provides for a food product made from a part of the lettuce variety Teton.

Another embodiment relates to a method of producing lettuce leaves as a food product which may comprise: sowing a seed of lettuce variety Teton, growing said seed into a harvestable lettuce plant and harvesting lettuce leaves or heads from the plant. Another embodiment further relates to packaging and/or processing the lettuce plants, heads or leaves. A further embodiment relates to method of producing lettuce leaves as a fresh vegetable comprising packaging the leaves of an Teton plant. Lettuce leaves can also be packaged into containers. Thus, another embodiment relates to a container which may comprise one or more lettuce plants of Teton for harvest of leaves.

Genetic Analysis of Lettuce Variety Teton.

Another embodiment further provides a method of determining a genetic characteristic of lettuce variety Teton or a progeny thereof, e.g., a method of determining a genotype of lettuce variety Teton or a progeny thereof. In embodiments, the method comprises detecting in the genome of an Teton plant, or a progeny plant thereof, at least a first polymorphism (e.g., using one or more molecular markers). To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. Another embodiment further provides a computer readable medium produced by such a method.

In addition to the exemplary aspects and embodiments described above, further aspects and embodiments will become apparent by study of the following descriptions.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One embodiment may be embodied in other specific forms without departing from its spirit or essential characteristics. The described embodiments are to be considered in all respects only as illustrative and not restrictive. All changes which come within the meaning and range of equivalency of the claims are to be embraced within their scope.

Various embodiments, include components, methods, processes, systems and/or apparatus substantially as depicted and described herein, including various embodiments, sub-combinations, and subsets thereof. Those of skill in the art will understand how to make and use an embodiment(s) after understanding the present disclosure.

The foregoing discussion of the embodiments has been presented for purposes of illustration and description. The foregoing is not intended to limit the embodiments to the form or forms disclosed herein. In the foregoing Detailed Description for example, various features of the embodiments are grouped together in one or more embodiments for the purpose of streamlining the disclosure. This method of disclosure is not to be interpreted as reflecting an intention that the embodiment(s) requires more features than are expressly recited in each claim. Rather, as the following claims reflect, inventive aspects lie in less than all features of a single foregoing disclosed embodiment. Thus, the following claims are hereby incorporated into the Detailed Description.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed.

DEPOSIT INFORMATION

A deposit of least 625 seeds of the Sakata Seed America, Inc. proprietary Lettuce variety Teton disclosed above and recited in the appended claims has been made with the Provasoli-Guillard National Center for Marine Algae and Microbiota, Bigelow Laboratory for Ocean Sciences (NCMA), 60 Bigelow Drive, East Boothbay, Maine 04544. The date the deposit was made was Sep. 15, 2021. The NMCA No. is 202109076. The deposit of plant tissue was taken from the same deposit maintained by Sakata Seed America, Inc. since prior to the filing date of this application. The deposit will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of 37 C.F.R. §§ 1.801-1.809.

The following claims are only examples of claims that may be made in a non-provisional application and are not exclusive, exhaustive, or limiting in any way. Further and additional claims may be presented in a non-provisional application to the extent such further or additional claims can be supported by any or all of the description and drawing in this provisional application. Therefore, example claims may include, but not be limited by, the following:

What is claimed is:

1. A plant, or a plant part thereof, or a seed of lettuce variety Teton, wherein a representative sample of seed of said variety is deposited under NCMA No. 202109076.

2. A lettuce plant, or a part thereof, of the plant or seed of claim 1, wherein the plant or plant part comprises at least one cell of lettuce variety Teton.

3. A tissue culture comprising at least one cell or protoplast of the plant or plant part of claim 2.

4. A method for producing a lettuce seed, wherein the method comprises fertilizing a lettuce plant and harvesting the resultant lettuce seed, wherein the lettuce plant is the lettuce plant of claim 1.

5. A lettuce seed produced by the method of claim 4, wherein the resulting lettuce seed is an F1 offspring or the product of self-fertilization.

6. A lettuce plant, or a part thereof, produced by growing the seed of claim 5.

7. A method of introducing a desired trait into lettuce variety Teton, wherein the method comprises introducing at least one mutation in a nucleic acid sequence of the lettuce plant, or plant part thereof, or seed of claim 1, wherein the mutation confers the desired trait to said lettuce plant, or said plant part thereof, or said seed.

8. A lettuce plant produced by the method of claim 7, wherein the plant comprises the desired trait and otherwise contains all of the morphological and physiological characteristics of lettuce variety Teton.

9. A method of producing a plant derived from lettuce variety Teton, wherein a representative sample of seed of said variety is deposited under NCIMB No. 202109076, comprising an added desired trait, wherein the method comprises introducing at least one nucleic acid sequence conferring the desired trait to said plant.

10. A lettuce plant produced by the method of claim 9, wherein the plant comprises the desired trait and otherwise contains all of the morphological and physiological characteristics of lettuce variety Teton.

11. The lettuce plant of claim 10, wherein the desired trait is selected from the group comprising male sterility, herbicide tolerance, pest tolerance, disease tolerance, modified fatty acid metabolism, modified carbohydrate metabolism, modified seed yield, modified seed oil, modified seed protein, modified lodging resistance, modified shattering, modified iron-deficiency chlorosis, modified water use efficiency, and/or combinations thereof.

12. A method of producing a plant product comprising collecting a plant product from the plant of claim 1, or plant part thereof.

13. A lettuce plant product produced by the method of claim 12, wherein the plant product is produced from a plant having at least one cell of lettuce variety Teton.

14. A method of introducing a desired trait into lettuce variety Teton, wherein the method comprises:
   a. crossing a Teton plant, wherein a sample of seed is deposited under NCMA No. 202109076, with a plant of another lettuce variety having a desired trait to produce progeny plants;
   b. selecting one or more progeny plants that have the desired trait to produce selected progeny plants;
   c. crossing the selected progeny plants with the Teton plant to produce backcross progeny plants;
   d. selecting for backcross progeny plants that have the desired trait; and
   e. repeating steps (c) and (d) a sufficient number of times in succession to produce selected second or higher backcross progeny plants that comprise the desired trait and otherwise all of the physiological and morphological characteristics of lettuce variety Teton.

15. A lettuce plant produced by the method of claim 14 wherein the plant has the desired trait.

16. A method for developing a lettuce plant, comprising applying plant breeding techniques to the plant of claim 1, or plant part thereof, comprising crossing, recurrent selection, mutation breeding, wherein said mutation breeding selects for a mutation that is spontaneous or artificially induced, backcrossing, genomic selection, pedigree breeding, marker enhanced selection, haploid/double haploid production, or transformation, wherein application of said techniques results in development of a new lettuce plant.

17. A method of introducing a mutation into the genome of lettuce variety Teton, said method comprising mutagenesis of the plant of claim 1, or a part thereof.

18. A method of editing the genome of lettuce variety Teton, said method comprising editing the genome of the plant, of claim 1, or plant part thereof, wherein said method is selected from the group comprising zinc finger nucleases, transcription activator-like effector nucleases (TALENs), engineered homing endonucleases/meganucleases, and the clustered regularly interspaced short palindromic repeat (CRISPR)-associated protein9 (Cas9) system.

19. A lettuce plant produced by the method of claim 18, wherein said plant is produced by editing the genome of said plant and otherwise contains all of the morphological and physiological characteristics of lettuce variety Teton.

20. The seed, or part thereof, of claim 1, wherein the seed further comprises at least one seed treatment.

21. A method of determining a genotype of lettuce variety Teton, the method comprising:
- obtaining a sample of nucleic acids from the plant of claim 2; and
- detecting in said nucleic acids one or more polymorphisms.

22. A method of producing lettuce leaves as a food product comprising sowing the seed of claim 1 and growing the seed into a harvestable lettuce plant and harvesting the head or leaves of said plant.

23. A method of producing lettuce leaves as a fresh vegetable comprising packaging the leaves of the plant of claim 2.

24. A container comprising one or more lettuce plants of claim 2 for harvest of leaves.

\* \* \* \* \*